United States Patent [19]

Howarth

[11] 4,297,345
[45] Oct. 27, 1981

[54] ANTIBACTERIAL AGENTS

[75] Inventor: Thomas T. Howarth, Ewhurst, England

[73] Assignee: Beecham Group Limited, England

[21] Appl. No.: 87,030

[22] Filed: Oct. 22, 1979

Related U.S. Application Data

[62] Division of Ser. No. 857,112, Dec. 5, 1977, which is a division of Ser. No. 669,697, Mar. 23, 1976.

[30] Foreign Application Priority Data

Apr. 14, 1975 [GB] United Kingdom ............... 15209/75
Sep. 27, 1975 [GB] United Kingdom ............... 39663/75

[51] Int. Cl.³ .............................................. A61K 35/00
[52] U.S. Cl. ..................................................... 424/114
[58] Field of Search ......................................... 424/114

Primary Examiner—Jerome D. Goldberg
Attorney, Agent, or Firm—Jacobs & Jacobs

[57] ABSTRACT

The compounds of the formula:

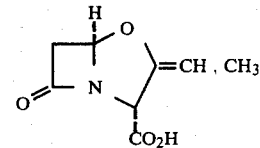

and salts and esters thereof are useful agents for the treatment of bacterial infections either alone or in combination with a penicillin or cephalosporin derivative. The preceding compounds may be prepared by the hydrogenation of a compound of the formula:

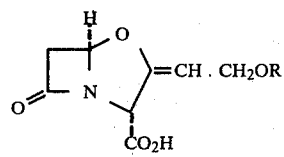

wherein R is a hydrogen atom or an acyl group or a salt or ester thereof.

17 Claims, No Drawings

ANTIBACTERIAL AGENTS

CROSS-REFERENCE

This is a division of Ser. No. 857,112 filed Dec. 5, 1977 which itself is a divisional of Ser. No. 669,697, filed Mar. 23, 1976.

The present invention relates to novel β-lactam containing compounds useful in anti-bacterial therapy, to compositions containing these novel compounds and to the method of their preparation.

Belgian Pat. No. 827926 discloses inter alia that the compound of the formula (I):

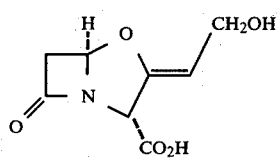

and its salts and esters possess anti-bacterial and β-lactamase inhibitory activity. The compound of the formula (I) is designated clavulanic acid. Acylated derivatives of the above compounds are disclosed in Netherlands Patent Application No. 75/12348 and West German Patent Application No. 2555626 discloses inter alia isoclavulanic acid and its salts and esters which compound isoclavulanic acid has the formula (II):

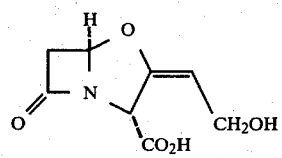

Isoclavulanic acid and its salts and esters also have antibacterial and β-lactamase inhibitory activity. A further group of compounds with useful anti-bacterial and β-lactamase inhibiting properties has now been discovered.

Accordingly the present invention provides the compounds of the formula (III):

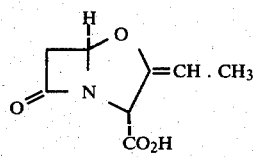

and salts and esters thereof.

The stereochemistry at C-2 and C-5 of the compounds of formula (III) is the same as that found in naturally occurring penicillins.

The two isomeric acids of the formulae (IV) and (V):

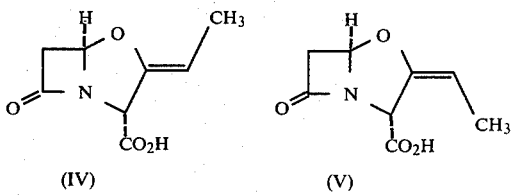

are therapeutic agents and are useful intermediates in the formation of their esters but in general their pharmaceutically acceptable salts are more favoured because of their improved stability. The compound of the formula (IV) is designated herein as deoxyclavulanic acid and the compound of the formula (V) is designated herein isodeoxyclavulanic acid.

In general deoxyclavulanic acid and its derivatives form a more favourable aspect of this invention than does isodeoxyclavulanic acid and its derivatives because of their generally more facile production.

Suitable salts of the compounds of the formula (III) include conventional pharmaceutically acceptable salts such as the sodium, potassium, calcium, magnesium, ammonium and conventional substituted ammonium salts formed with benzylpenicillin such as the 1-ephenamine, procaine, benzathine and the like salts.

Particularly suitable salts of deoxyclavulanic acid and isodeoxyclavulanic acid include their sodium and potassium salts.

Preferred salts of this invention include those of the formulae (VI) and (VII):

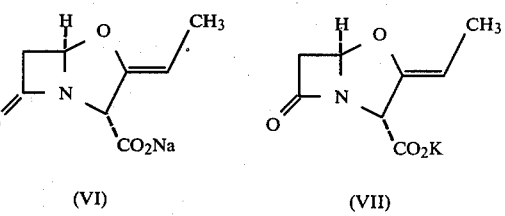

The sodium salt of deoxyclavulanic acid is a particularly suitable compound of this invention.

Non-pharmaceutically acceptable salts of the compounds of the formula (III) can also be useful as they can serve as intermediates in the preparation of esters of the compounds of formula (III); for example, by reaction with pivaloyloxymethyl chloride to give a useful antibacterial agent.

Suitable esters of the compounds of formula (III) include those of the formula (VIII):

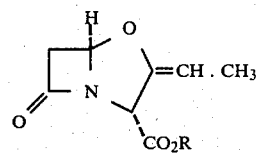

wherein R is an organic group such that the alcohol ROH is pharmaceutically acceptable.

It is envisaged that the esters of deoxyclavulanic acid and deoxyisoclavulanic acid owe much of their antibacterial activity to their ability to act as pro-drugs for deoxyclavulanic and isodeoxyclavulanic acids and their salts. Thus preferred esters are those which are convertible to the corresponding acid or its salts under physiological conditions.

Particularly suitable esters of the compounds of the formula (VIII) include those of the formula (IX):

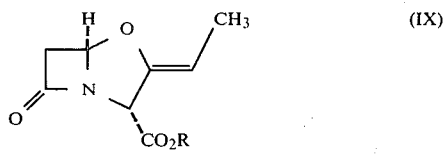
(IX)

wherein R is as defined in relation to formula (VIII).

Suitable groups R for inclusion in the compounds of formula (VIII) and (IX) include alkyl, alkenyl, alkynyl, aryl, arylalkyl or other similar groups any of which may be substituted if desired.

In order not to increase the molecular weight to an unreasonable extent, groups R do not normally include more than 16 carbon atoms, more suitably not more than 12 carbon atoms and most suitably, not more than 8 carbon atoms. Generally the $CO_2R$ group is such that the compound of the formula (VIII) has a molecular weight of not more than 400.

Preferably, the group R is notionally derived from an alcohol ROH which is pharmaceutically acceptable. Suitable groups R include methyl, ethyl, propyl, butyl, pentyl, hexyl, heptyl, octyl, nonyl, decyl, undecyl, dodecyl, vinyl, allyl, butenyl, cyclopropyl, cyclobutyl, cyclopentyl, cyclohexyl, cycloheptyl, cyclohexenyl, cyclohexadienyl, methylcyclopentyl, methylcyclohexyl, cyclopentylmethyl, cyclohexylmethyl, benzyl, benzhydryl, phenylethyl, naphthylmethyl, naphthyl, phenyl, propynyl, tolyl, 2-chloroethyl, 2,2,2-trichloroethyl, 2,2,2-trifluoroethyl, acetylmethyl, benzoylmethyl, 2-methoxyethyl, p-chlorobenzyl, p-methoxybenzyl, p-nitrobenzyl, p-bromobenzyl, m-chlorobenzyl, 6-methoxynaphthyl-2-methyl, p-chlorophenyl, p-methoxyphenyl, $\beta$-2'-pyridylethyl or like group.

Suitable readily in-vivo hydrolysable ester groups $CO_2R$ include but are not limited to acyloxyalkyl and lactone groups such as those represented by the sub-formulae (a) and (b):

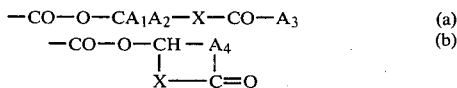

wherein $A_1$ is a hydrogen atom or a methyl group; $A_2$ is a hydrogen atom or a methyl, ethyl or phenyl group; $A_3$ is an alkyl or alkoxyl group of 1-6 carbon atoms or a phenyl or benzyl group; $A_4$ is —$CH_2CH_2$—, —CH:-CH—,

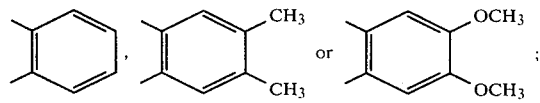

and X is an oxygen or sulphur atom. Most suitably X is an oxygen atom and $A_2$ is a methyl or t-butyl group and $A_4$ is a phenylene group.

A further particularly suitable sub-group of esters of formulae (VIII) or (IX) are those wherein R is a group $R^1$ or $CHR^2R^3$ wherein $R^1$ is a hydrocarbon group of 1-9 carbon atoms optionally substituted by halogen, lower alkoxy, lower acyl, hydroxy or lower acyloxy groups and $R^2$ is an optionally substituted phenyl group and $R^3$ is an optionally substituted phenyl group.

The term 'lower' used herein means the group contains up to 6 carbon atoms. The term 'optionally substituted phenyl' includes a phenyl group and a phenyl group substituted by a halogen atom or a lower alkyl or lower alkoxy group.

An alternative aspect of the present invention provides a pharmaceutical composition which contains a compound of the formula (III) or a pharmaceutically acceptable salt or ester thereof and a pharmaceutically acceptable carrier. Favourably such compositions contain a pharmaceutically acceptable salt or in-vivo hydrolysable ester of a compound of the formula (III).

More suitably, the pharmaceutical composition of this invention will contain a pharmaceutically acceptable salt of the compound of the formula (III). The compositions of this invention will normally be adapted for administration to humans and other mammals, for example, in conventional modes of treatment of diseases of the urinary tract, respiratory system and soft tissues as well as diseases such as otitis media in humans and mastitis in domestic animals and the like.

Suitable forms of the compositions of this invention include tablets, capsules, creams, syrups, suspensions, solutions, reconstitutable powders and sterile forms suitable for injection or infusion may be used. Such compositions may contain conventional pharmaceutically acceptable materials such as diluents, binders, colours, flavours, preservatives, disintegrants and the like in accordance with conventional pharmaceutical practice and the arts of formulating antibiotic compositions.

Compositions adapted for oral administration may also comprise a buffering agent or may be protected from gastric juice in other conventional manner if so desired.

The compound of formula (III) may be present in the composition as sole therapeutic agent or it may be present together with other therapeutic agents such as a $\beta$-lactam antibiotic. Suitable $\beta$-lactam antibiotics for inclusion in such compositions include not only those known to be susceptible to $\beta$-lactamases but also those which have a degree of intrinsic resistance to $\beta$-lactamases. Thus, suitable $\beta$-lactam antibiotics for inclusion in the composition of this invention include benzylpenicillin, phenoxymethylpenicillin, carbenicillin, methicillin, propicillin, hetacillin, ampicillin, amoxycillin, ticarcillin, cephaloridine, cephalothin, cephalexin, cephaloglycin, cephamandole and in-vivo hydrolysable esters of such compounds such as the phenyl, tolyl and 5-indanyl esters of carbenicillin and ticarcillin, the acetoxymethyl ester of benzylpenicillin and the acetoxymethyl, pivaloyloxymethyl and phthalidyl esters of ampicillin, amoxycillin, cephaloglycin, cephalexin, mecillinam and the like or salts of such compounds.

When present in a pharmaceutical composition together with a $\beta$-lactam antibiotic, the ratio of the compound of formula (III) or its salt or ester present to $\beta$-lactam antibiotic present may be from, for example, 20:1 to 1:5, such as 10:1 to 1:3, and advantageously may be 5:1 to 1:2, for example, 3:1 to 1:1.

The total quantity of antibacterial agents present in any unit dosage form will normally be between 50 and 1500 mg and will usually be between 100 and 1000 mg. However, injectable or infusable compositions may contain greater quantities if desired, for example, 4 g or more of active material. Normally, between 50 and 6000 mg of the compositions of this invention will be administered each day of treatment but more usually between 500 and 3000 mg of the composition of the invention will be administered per day. In general the equivalent of not more than 2000 mg of a compound of the formula (III) will be administered per day, for example, 100–1000 mg.

In a further aspect this invention provides synergistic compositions which contain a compound of the formula (III) or a pharmaceutically acceptable salt or ester thereof and ampicillin, amoxycillin or a pro-drug for ampicillin or amoxycillin. Such compositions are preferably adapted for administration to humans and contain 50–500 mg of a salt or in-vivo hydrolysable ester of a compound of the formula (III) and 200–1000 mg of the penicillin. Particularly suitable forms of the penicillins for inclusion in orally administrable forms of such compositions include ampicillin trihydrate, amoxycillin trihydrate, acetylamoxycillin trihydrate, anhydrous ampicillin, ampicillin pivaloyloxymethyl ester and ampicillin phthalidyl ester or salts such as the hydrochloride of such esters. Particularly suitable forms of the penicillins for inclusion in injectable forms include sodium ampicillin and sodium amoxycillin, sodium ampicillin being preferred. Such compositions may be used in treating infections of the urinary tract and respiratory tract and are particularly useful in treating infections due to strains of *Klebsiella aeroginosa*, Proteus, or *E. coli*.

In a further aspect this invention provides synergistic compositions which contain a compound of the formula (III) or a pharmaceutically acceptable salt or ester thereof and carbenicillin or ticarcillin or their salts or a pro-drug for carbenicillin or ticarcillin such as carbenicillin phenyl$\alpha$-ester, carbenicillin 5-indanyl$\alpha$-ester, ticarcillin phenyl$\alpha$-ester or ticarcillin tolyl$\alpha$-ester or their salts. Such compositions are preferably adapted for administration to humans and contain 50–1500 mg of a salt or in-vivo hydrolysable ester of a compound of the formula (III) and 200–1500 mg of the penicillin. Such compositions may be used in treating infections of the urinary tract.

The preceding compositions preferably contain a pharmaceutically acceptable salt of a compound of the formula (III) such as the sodium or potassium salt, for example, a compound of the formula (VI).

In a further aspect this invention provides a process for the preparation of a compound of the formula (III) as hereinbefore defined or a salt or ester thereof which process comprises the hydrogenation of a corresponding compound of the formula (X):

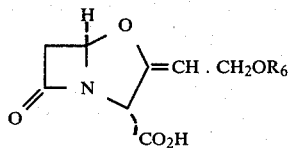

(X)

or a salt or ester thereof wherein $R_6$ is a hydrogen atom or an acyl group.

It is frequently particularly convenient to use a compound of the formula (X) wherein $R_6$ is a hydrogen atom. It is also frequently convenient to use a compound of the formula (X) in the form of a salt thereof.

Normally, such a reaction takes place in the presence of a transition metal containing catalyst such as palladium, platinum oxide or the like. A particularly suitable catalyst is palladium on charcoal, for example, 10% palladium on charcoal.

The catalyst employed is suitably in highly active form, for example, the sort obtained by using a fresh batch of catalyst.

Most suitably the weight of catalyst (as total 10% palladium and charcoal or the equivalent) present is at least $\frac{1}{3}$ of the weight of the compound of formula (X) or salt or ester present. It is advantageous to have at least as much catalyst present as compound of formula (X) present, especially for those compounds wherein $R_6$ is H.

The process of this invention normally takes place at a non-extreme temperature; for example, the reaction may take place in a lower alkanol at a temperature of $-10°$ C. to $+50°$ C., more usually from $0°$ C. to $25°$ C., for example, from $5°$ C. to $20°$ C.

The process of this invention normally takes place in an inert solvent such as a lower alkanol, water or an aqueous alkanol. Most suitably the solvent employed is a lower alkanol such as methanol or ethanol. For those compounds of the formula (X) wherein $R_6$ is H water miscible ethers such as tetrahydrofuran are also suitable solvents but such ether solvents are not generally suitable for use when $R_6$ is an acyl group.

An elevated, medium or low pressure of hydrogen may be used in this reaction. Generally, it is preferred to use an atmospheric or slightly super atmospheric pressure of hydrogen.

A preferred form of the process of this invention comprises the hydrogenation of clavulanic acid or a salt or hydrogenisable ester thereof in the presence of a palladium catalyst. Such a process leads to the preparation of a compound of the formula (IV) or a salt thereof. If a salt is required and the clavulanic acid is not already in salt form a base such as sodium bicarbonate or the like may be included in the reaction medium.

Hydrogenation of isoclavulanic acid or a derivative thereof frequently leads to a deoxyisoclavulanic acid derivative contaminated with a corresponding deoxyclavulanic acid derivative. A purer product may then be obtained by chromatography.

The nature of the acyl group $R_6$ which may be present in a compound of the formula (X) is relatively unimportant as long as it does not lead to the rapid breakdown of the compound of formula (X). Suitable acyl derivatives are described in Netherlands Application No. 75/12348. Particularly suitable acyl groups $R_6$ contain up to 16 carbon atoms and may be optionally substituted by groups such as halogen, lower alkoxy, lower alkoxycarbonyl, lower acyloxy, hydroxy and the like. Most suitably such acyl groups are unsubstituted or substituted by non-reactive groups only.

Esters of the compounds of formula (III) may be prepared by the reaction of a compound of the formula (III) or a salt thereof with an alcohol ROH or a compound of the formula RQ where Q is a good leaving group such as a chlorine, bromine or iodine atom or an activated ester group or a sulphonic ester such as a mesylate or tosylate group or other conventional good leaving group. Alternatively, the acid of the formula (III) may be treated with a diazocompound such as diazomethane or the like or with an alcohol ROH in the presence of a dehydrating agent such as a carbodiimide or its chemical equivalent.

The reaction with RQ¹ is normally carried out in an organic solvent of relatively high dielectric constant such as dimethylformamide, acetone, dioxane, tetrahydrofuran or the like and at a non-extreme temperature such as −5° C. to 100° C., more usually +5° C. to 30° C., for example, at ambient temperature.

The reaction of an acid of formula (III) with a diazoalkane is a mild method of making alkyl, aralkyl or similar esters. The diazotization reaction may be performed under conventional reaction conditions, for example at a non-extreme temperature and in a conventional solvent. Such reactions are normally carried out at between −5° C. and 100° C., more usually from 5° C. to 30° C., for example at ambient temperature. Suitable solvents for this reaction include lower alkanols such as methanol and ethanol and solvents such as tetrahydrofuran, dioxane and the like. Ethanol has proved a particularly useful solvent for this reaction.

The reaction of an acid of formula (III) with an alcohol in the presence of a condensation promoting agent will normally take place in an inert organic solvent such as dichloromethane or acetonitrile. This reaction is usually carried out at an ambient or depressed temperature, for example at −10° C. to +22° C., more usually −5° C. to +18° C., for example initially at 0° C. and thereafter gradually warming to about 15° C. The condensation promoting agent used is normally one which removes water from the reaction mixture. Suitable agents include carbodiimides, carbodiimidazoles or equivalent reagents. Dicyclohexylcarbodiimide has proved to be a particularly suitable condensation promoting agent for use in this process.

Other less suitable methods of ester formation include (a) removal of the elements of carbon dioxide from a compound of the formula (XI):

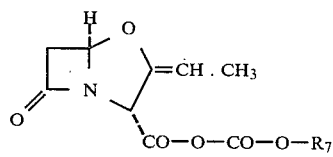

(XI)

wherein R₇ is an inert organic group; and also (b) reaction of a compound of the formula (XI) with alcohol ROH.

The compound of the formula (XI) may be prepared by the reaction of a salt of a compound of the formula (III) with Cl.CO.O.R₇ or the chemical equivalent thereof.

Salts of the compounds of the formula (III) may be prepared by the hydrolysis of an ester of a compound of the formula (III). Generally this may be brought about by keeping the ester of the compound of formula (III) in an aqueous medium maintained at pH of about 7–9 for up to one hour. Certain reactive esters such as the pivaloyloxymethyl, acetoxymethyl, phthalidyl and like esters hydrolyse in a few minutes when maintained in an aqueous medium at a pH of about 6–8.

The following Examples illustrate the invention:

EXAMPLE 1

Sodium Deoxyclavulanate

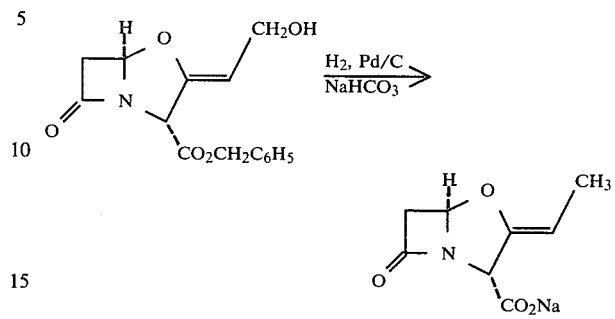

Benzyl clavulanate (220 mg) in ethanol (20 ml) was hydrogenated over 10% Pd/C (70 mg) and sodium hydrogen carbonate (60 mg) for 60 minutes. The catalyst was filtered, washed with water and then ethanol and the combined filtrates were evaporated. This material was chromatographed on a silica gel column with n-butanol/ethanol/water; 4:1:1¾ and the fastest moving component was collected. The solvents were removed under low pressures to yield the sodium salt of deoxyclavulanic acid.

I.r. (KBr): 1780, 1700, 1605 cm⁻¹; n.m.r. (D₂O): 1.52 (3H, dd, J 7 Hz, J' 1.5 Hz); 2.98 (1H, d, J 18 Hz, 6β-C$\underline{H}$); 3.52 (1H, dd, J 18 Hz, J' 2.5 Hz, 6α-C$\underline{H}$); 4.5–4.9 (m, obscured by HOD peak); 5.64 (1H, d, J 2.5 Hz, 5-C$\underline{H}$).

(The sodium salt of clavulanic acid was also obtained from the column on further elution).

EXAMPLE 2

Sodium Deoxyclavulanate

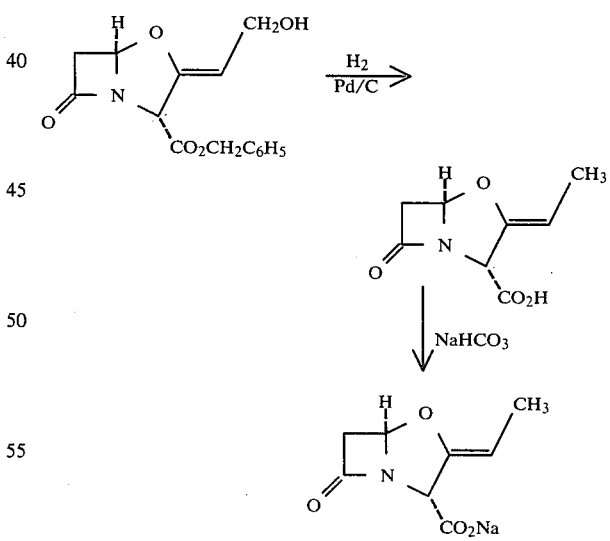

Benzyl clavulanate (8.25 g) was dissolved in tetrahydrofuran (75 ml). To the solution was added 10% palladium on charcoal (8.25 g) and the mixture was hydrogenolysed at room temperature with vigorous shaking and using 1 atmosphere pressure of hydrogen for 30 minutes. The suspension was filtered and the filtrate was treated with a solution of sodium bicarbonate (2.39 g) dissolved in the minimum amount of water. The solution was concentrated under reduced pressure on a rotary evaporator at room temperature and the residue was triturated with acetone and ether to give a pale yellow solid (4.7 g).

EXAMPLE 3

Sodium Deoxyclavulanate

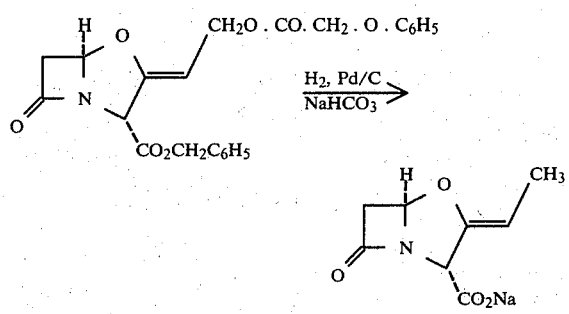

Benzyl phenoxyacetylclavulanate (140 mg) was dissolved in ethanol/ethyl acetate (5:1, 6 ml) and sodium bicarbonate (56 mg) and 10% palladium on charcoal (47 mg) were added to the solution. The solution was hydrogenated at ambient temperature (~18° C.) for 15 minutes. The catalyst was filtered off and washed well with water. The filtrate and washings were combined and evaporated to dryness to give a quantitative yield of sodium deoxyclavulanate. Sodium deoxyclavulanate may be separated from the mixture with sodium phenoxyacetate by careful column chromatography using silica gel and eluting with butanol/ethanol/water. (Physical characteristics of product as in Example 1).

The preceding example may be varied by replacing the benzyl phenoxyacetylclavulanate with equivalent amounts of benzyl acetylclavulanate, benzyl α-phenyloxycarbonylphenylacetylclavulanate, p-bromobenzyl phenoxyacetylclavulanate and the like. The preceding example may also be varied by replacing the benzyl phenoxyacetylclavulanate with an equivalent amount of benzyl α-benzyloxycarbonylphenylacetamidoclavulanate and increasing the amount of sodium bicarbonate to 2 equivalents.

EXAMPLE 4 p-Bromobenzyl Deoxyclavulanate

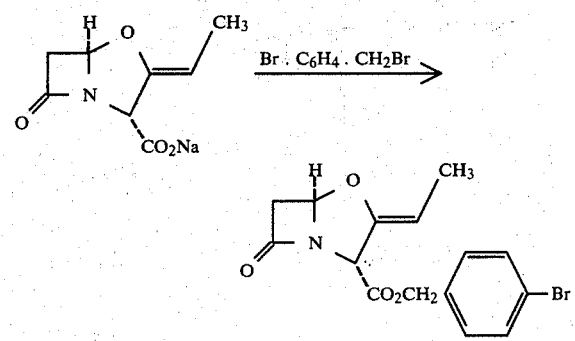

A solution of p-bromobenzyl bromide (50 mg) was added to a solution of sodium deoxyclavulanate (10 mg) in dimethylformamide (0.5 ml) and the mixture was kept at ambient temperature (about 18° C.) for 2 hours. The reaction mixture was fractionated on silica gel eluting with ethyl acetate/hexane (1:4) to yield p-bromobenzyl deoxyclavulanate (as an oil) on evaporation.

I.r. (CHCl$_3$): 1790, 1740, 1695 cm$^{-1}$; N.m.r. (CDCl$_3$): 1.62 (3H, dd, J 7 Hz, J' 1.4 Hz, CH$_3$); 2.95 (1H, dd, J 17 Hz, J' 1.0 Hz, 6β-CH); 3.48 (1H, dd, J 17 Hz, J' 2.6 Hz, 6α-CH); 4.58 (1H, dq, J 7 Hz, J' 1 Hz, =CHCH$_3$); 5.03 (1H, dd, J 1.4 Hz, J' 1.0 Hz, 3-CH); 5.12 (2H, s, CO$_2$CH$_2$—); 5.65 (1H, dd, J 2.6 Hz, J' 1.0 Hz, 5-CH); 3.38 (4H, ABq, J 8.5 Hz, aromatic protons).

The preceding example may be repeated replacing p-bromobenzyl bromide with an equivalent quantity of methyl iodide, ethyl bromide, 1-bromo-2-methoxyethane, pivaloyloxymethyl chloride, phthalidyl bromide, 1-chloro-2-thiomethylethane, 1-chloro-2-phenylsulphonylethane, 1-bromononane, 4-methoxybenzylbromide, benzylbromide, benzylchloride, phenacetyl bromide or the like.

EXAMPLE 5

Sodium Deoxyisoclavulanate

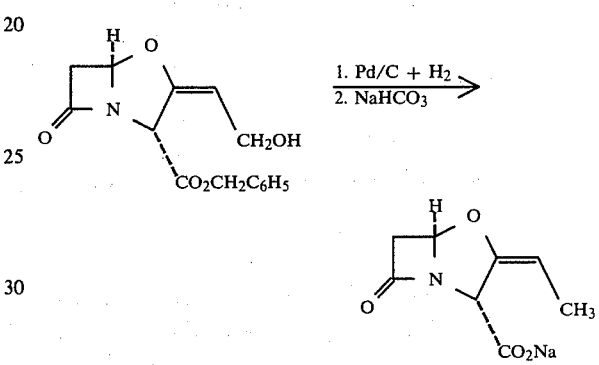

Benzyl isoclavulanate (50 mg) in tetrahydrofuran (0.5 ml) was hydrogenated at room temperature (~18° C.) and atmospheric pressure using 10% palladium on charcoal (50 mg) as catalyst. After 30 minutes the catalyst was filtered off and an equivalent amount of aqueous sodium bicarbonate added. The solvent was removed by evaporation and the residue triturated with ethanol, acetone and acetone/ether to give the product as an off-white solid (20 mg). (The n.m.r. spectrum in D$_2$O showed that the title compound was contaminated with sodium deoxyclavulanate).

EXAMPLE 6

Pharmacology

Sodium deoxyclavulanate did not appear to produce any overt toxic effects in mice when administered intraperitoneally at 500 mg/kg.

The antibacterial and synergistic properties of sodium deoxyclavulanate are illustrated by the following in-vitro results:

| Organism | Minimum Inhibitory Concentration of Sodium Deoxyclavulanate (μg/ml) |
| --- | --- |
| Bacillus subtilis A | 62.5 |
| Enterobacter cloacae N1 | 125 |
| Escherichia coli 10418 | 62.5 |
| Klebsiella aerogenes A | 62.5 |
| Proteus mirabilis C 977 | 125 |
| Pseudomonas aeruginosa A | 1000 |
| Salmonella typhimurium CT10 | 125 |
| Serratia marcescens US 39 | 125 |
| Staph. aureus Oxford | 15.6 |
| Staph. aureus Russell | 31 |

| Organism | Minimum Inhibitory Concentration (μg/ml) of Ampicillin in Presence of Various Concentrations of Sodium Deoxyclavulanate (μg/ml) | | | |
| --- | --- | --- | --- | --- |
| | 0 | 1 | 5 | 20 |
| *Staphylococcus aureus* Russell | 500 | 0.8 | 0.08 | * |
| *Klebsiella aerogenes* E70 | >500 | 0.8 | 0.2–0.4 | 0.1–0.02 |

*Inhibition produced by sodium deoxyclavulanate alone at this concentration

What is claimed is:

1. A pharmaceutical composition for treating bacterial infections in humans and animals which comprises a synergistically effective amount of a compound of the formula (III):

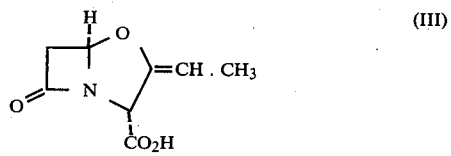

or a pharmaceutically acceptable salt thereof, and an antibacterially effective amount of benzylpenicillin or the acetoxymethyl ester thereof, in combination with a pharmaceutically acceptable carrier, the weight ratio of said compound or pharmaceutically acceptable salt thereof to benzylpenicillin or said ester thereof being 20:1 to 1:5.

2. A composition according to claim 1 wherein the compound is in the form of a pharmaceutically acceptable salt wherein said salt is selected from the group consisting of the sodium, potassium, calcium, magnesium, ammonium, ephenamine, procaine and benzathine salts.

3. A composition according to claim 1 wherein the pharmaceutically acceptable salt is of the formula (IV) or (V):

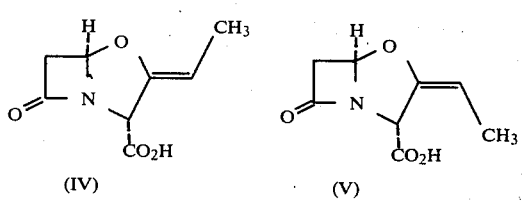

4. A composition according to claim 3 wherein the salt is the sodium or potassium salt of compound (IV) or (V).

5. A composition according to claim 1 wherein the compound is in the form of a salt of the formula (VI) or (VII):

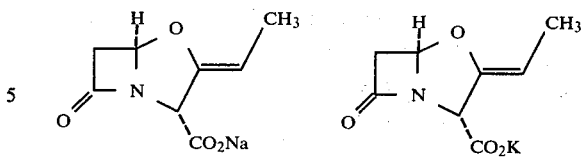

6. A composition according to claim 5 wherein the compound is in the form of the sodium salt of the compound (VI).

7. A composition according to claim 1 wherein the ratio is 10:1 to 1:3.

8. A composition according to claim 1 wherein the ratio 5:1 to 1:2.

9. A composition according to claim 1 wherein the ratio 3:1 to 1:1.

10. A method of treating bacterial infection in humans and animals which comprises administering to humans or animals in need thereof synergistically effective amount of a compound of the formula (III):

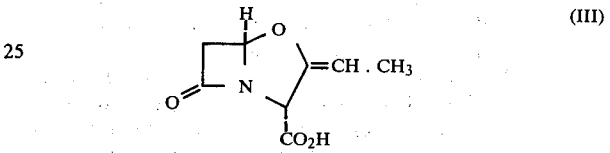

or a pharmaceutically acceptable salt thereof, and an antibacterially effective amount of benzylpenicillin or the acetoxymethyl ester thereof, the weight ratio of said compound or pharmaceutically acceptable salt thereof and said benzylpenicillin or ester thereof being 20:1 to 1:5.

11. A method according to claim 10 wherein the compound is a pharmaceutically acceptable salt of the formula (IV) or (V):

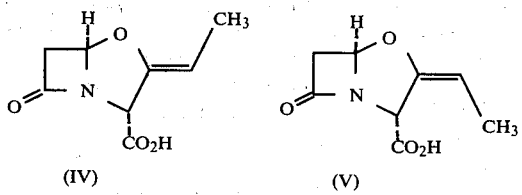

12. A method according to claim 11 wherein the compound is a sodium or potassium salt.

13. A method according to claim 10 wherein the compound is a salt of the formula (VI) or (VII):

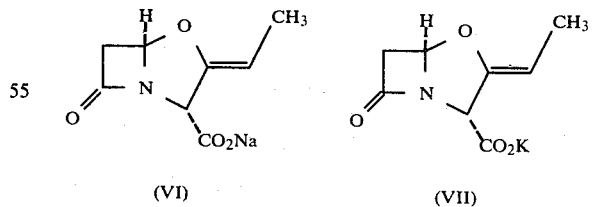

14. A method according to claim 13 wherein the compound is a sodium salt of the formula (VI).

15. A method according to claim 10 wherein the ratio is 10:1 to 1:3.

16. A method according to claim 10 wherein the ratio 5:1 to 1:2.

17. A method according to claim 10 wherein the ratio 3:1 to 1:1.

* * * * *